(12) United States Patent
Giger

(10) Patent No.: US 11,510,821 B2
(45) Date of Patent: Nov. 29, 2022

(54) SCAR REDUCTION BANDAGE

(71) Applicant: Adrian Giger, Lommiswil (CH)

(72) Inventor: Adrian Giger, Lommiswil (CH)

( * ) Notice: Subject to any disclaimer, the term of this patent is extended or adjusted under 35 U.S.C. 154(b) by 459 days.

(21) Appl. No.: 16/337,560

(22) PCT Filed: Sep. 29, 2017

(86) PCT No.: PCT/IB2017/056030
§ 371 (c)(1),
(2) Date: Mar. 28, 2019

(87) PCT Pub. No.: WO2018/060958
PCT Pub. Date: Apr. 5, 2018

(65) Prior Publication Data
US 2019/0343688 A1    Nov. 14, 2019

(30) Foreign Application Priority Data
Sep. 30, 2016    (CH) .................................. 01302/16

(51) Int. Cl.
*A61F 13/02*    (2006.01)
*A61F 13/00*    (2006.01)

(52) U.S. Cl.
CPC .... *A61F 13/0243* (2013.01); *A61F 13/00063* (2013.01); *A61F 13/0253* (2013.01); *A61F 2013/0028* (2013.01); *A61F 2013/00119* (2013.01)

(58) Field of Classification Search
CPC .... A61F 2013/0028; A61F 2013/00119; A61F 2005/0179; A61F 2005/0197; A61F 5/26; A61F 5/30; A61F 13/00063; A61F 13/0243; A61F 13/0253; A61F 13/023; A61L 15/44; A61L 15/26; A61L 15/14
See application file for complete search history.

(56) References Cited

U.S. PATENT DOCUMENTS

| | | | |
|---|---|---|---|
| 5,759,560 A | 6/1998 | Dillon | |
| 5,919,476 A | 7/1999 | Fischer et al. | |
| 6,284,941 B1 | 9/2001 | Cox et al. | |
| 6,822,132 B2 | 11/2004 | Ahrens et al. | |

(Continued)

FOREIGN PATENT DOCUMENTS

| | | | |
|---|---|---|---|
| DE | 19808228 B4 * | 4/2009 | ............. A61F 5/028 |
| EP | 0 081 109 A2 | 11/1982 | |

(Continued)

OTHER PUBLICATIONS

US 6,389,791 B1, 03/2013, Gurtner et al. (withdrawn)

(Continued)

*Primary Examiner* — Benjamin J Klein
(74) *Attorney, Agent, or Firm* — Merchant & Gould P.C.

(57) ABSTRACT

The invention relates to an easy-to-use scar reduction bandage (or sticking plaster), that can be used in the case of hypertrophic scars and keloids. The invention offers a qualitatively even treatment over months by the permanent pressure achieved by the integrated scar bandage and spring. The effect can be strengthened or altered by the differing materials of upper and lower carrier sheets. Likewise, and at the same time, a supplemental treatment can be initiated by so-called storage structures in the base of the spring.

32 Claims, 8 Drawing Sheets

(56) References Cited

U.S. PATENT DOCUMENTS

| | | | |
|---|---|---|---|
| 6,843,778 B2 | 1/2005 | Foeldes | |
| 7,115,792 B2 | 10/2006 | Kartheus et al. | |
| 8,338,657 B1 * | 12/2012 | Walls | A61F 13/0246 602/43 |
| 2002/0156411 A1 | 10/2002 | Ahrens et al. | |
| 2004/0167461 A1 | 8/2004 | Nitzan et al. | |
| 2005/0095276 A1 | 5/2005 | Kartheus et al. | |
| 2008/0103462 A1 * | 5/2008 | Wenzel | A61N 1/205 604/313 |
| 2009/0198222 A1 | 8/2009 | Cho | |
| 2014/0316323 A1 * | 10/2014 | Kanevsky | A61F 13/0243 602/53 |
| 2015/0012037 A1 * | 1/2015 | Goldman | A61F 13/02 606/216 |
| 2016/0158066 A1 * | 6/2016 | Chao | A61F 13/00068 604/304 |
| 2017/0181882 A1 * | 6/2017 | Chisena | A61F 5/05833 |
| 2018/0353335 A1 * | 12/2018 | Walker | A61F 13/0213 |
| 2019/0133582 A1 * | 5/2019 | Eaves | A61F 13/00068 604/304 |

FOREIGN PATENT DOCUMENTS

| | | | |
|---|---|---|---|
| EP | 0 919 211 A2 | 6/1999 | |
| EP | 2 210 619 A2 | 7/2010 | |
| EP | 2210619 A2 * | 7/2010 | A61L 15/26 |
| EP | 1 490 118 B1 | 9/2010 | |
| EP | 2 258 406 A2 | 12/2010 | |
| EP | 1 190 722 A2 | 3/2012 | |
| WO | 98/17287 A1 | 4/1998 | |
| WO | 03/080133 A1 | 10/2003 | |
| WO | 2008/019051 A2 | 2/2008 | |
| WO | WO-2011119760 A2 * | 9/2011 | A61K 9/7084 |

OTHER PUBLICATIONS

Written opinion of the International Searching Authority issued in PCT/IB2017/056030 completed on Dec. 6, 2017.

International Search Report issued in PCT/IB2017/056030 completed on Dec. 6, 2017 and dated Dec. 14, 2017.

Therapie pathologischer Narben (hypertrophe Narben and Keloide, AWMF-REgister Nr. 013/030 (AWMF online, Apr. 2012).

* cited by examiner

_US 11,510,821 B2_

SCAR REDUCTION BANDAGE

This application claims priority from Swiss Patent Application No. 01302/16, filed Sep. 30, 2016, the entire disclosure of which is incorporated herein by reference.

FIELD OF THE INVENTION

The invention relates to a scar dressing with integrated, force applying, spring pressure. The invention encompasses a scar dressing with a breathable and preferably adhesive polyurethane matrix with preferably a carrier film made preferably with water vapor permeable and water impermeable polymer sheet or other sheet. In order to apply sufficient pressure on the scar tissue, an integrated spring is built into the dressing or bandage. Scar bandages are used over a great length of time, and not steadily changed, like wound treating wraps or bandages.

BACKGROUND OF THE INVENTION

The best confirmed treatment of hypertrophic scars and keloids is pressure treatment. The dressing or bandage effects a permanent pressure on the scar tissue. Normal bandages or dressings cannot effect a sufficiently large pressure on the scar tissue. The scar reducing bandage with integrated spring according to the present invention can locally apply sufficient force to the scar tissue permanently.

WO 2003080133 describes a bandage for the reduction of scars. The scar reducing bandage encompasses a carrier film of air and water vapor permeable and water impermeable polymer sheet, a scar dressing made of breathable and adhesive Polyurethane-xerogel-matrix, wherein the carrier film is layered its entire surface with a polyurethane matrix and the edge sheet is made of the same polyurethane-xerogel-matyrix that bevels to the edge with a thickness of maximally 5 to 150 µm.

EP 2 210 619 A2 describes a scar dressing with UV protection.

EP 0 081 109 A2 describes a bandage with permanent magnets for treating larger surface areas for issues including rheumatism, joint pain, sciatica, and scars.

EP 0 919 211 A2 describes a wound dressing with a carrier film including a cavity dosed with a gel material for treating blisters or ulcers.

EP 1 490 118 B1 describes a scar-reducing dressing with a support film that prevents the edges of the dressing from detaching from the skin and rolling up.

EP 2 258 406 A2 describes a scar-reducing silicone dressing with a silicone layer including holes for controlling the dissipation of moisture of the skin wounds to prevent the acidic metabolite in perspiration from touching the skin for long periods of time and causing irritation.

U.S. Pat. No. 5,759,560 describes a scar-reducing composite material with a soft silicone elastomer layer bonded to a thermoplastic sheet that can be shaped to fit anatomical contours.

U.S. Pat. No. 5,919,476 describes a scar-reducing bandage with a reinforced silicone gel sheet designed to adhere to skin, and another layer of non-adherent silicone with a layer of polyester mesh with a plurality of holes effectively laminated between to silicone layers.

U.S. Pat. No. 6,284,941 describes a scar-reducing bandage using silicone sheeting or silicone gel.

U.S. Pat. No. 6,843,778 describes a flexible surgical plaster for healing skin injuries and reducing scars with a polarizing window that allows treatment of the skin surface with polarized light through the bandage.

U.S. Pat. No. 8,389,791 describes a bandage for ameliorating scar formation by shielding the wound from endogenous or exogenous stress.

US 2004/0167461 describes a patch with an electrochemical cell with two electrodes and a retainer for conductive fluid, for transdermal or intradermal delivery of a substance to the skin.

US 2005/0095276 describes a scar-reducing plaster with a backing film, a polymer layer, and a polyurethane xerogel matrix layer that coats the backing film, designed to have a reduced tendency to peel off the skin during normal use.

US 2009/0198222 describes dermal scar treatment equipment including a pad that electrically connects with a high frequency generator, a plurality of pins for inserting into the collagen fibers of the dermis through the epidermis, and an insulating layer to isolate the pins from the epidermis.

US 2015/0012037 describes a pres-stressed pressure device for treating a wound or scar with a pressure member having a curved central portion that, when pressed down at the ends, applies pressure to the wound or scar. The document admits that the maximum pressure achieved is no more than about 0.003 $N/mm^2$, less than that of the present invention.

The paper, _Therapie pathologischer Narben_ (_hypertrophe Narben and Keloide_, AWMF-REgister Nr. 013/030 (AWMF online, April 2012), describes general recommendations for the treatment of keloids and scars.

SUMMARY OF THE INVENTION

The present invention has an objective to overcome the shortcomings of the prior art and provide a easily usable dressing for reducing hypertrophic scars and keloids. It must be skin protective, durably adhesive, and easily removable and applicable. The scar dressing or bandage with an integrated pressure applying spring is, through its spring construction, shielded from UV light and simultaneously applies a force to the scar tissue. An advantage of the present invention is that a pressure is permanently applied to the user's scar tissue by the spring base at a minimum force of 0.003 $N/mm^2$, preferably 0.005 $N/mm^2$, more preferable 0.01 $N/mm^2$, and even more preferably 0.02 $N/mm^2$. A maximum force applied to the user's scar tissue is not limited.

The scar dressing according to the present invention reliably and comprehensively protects fresh scar tissue from damaging influences.

BRIEF DESCRIPTION OF THE DRAWINGS

The present invention will be described subsequently in more detail with reference to the attached drawings, given by way of examples, but in no way limited thereto, in which.

DETAILED DESCRIPTION OF THE INVENTION

Figure 9A:
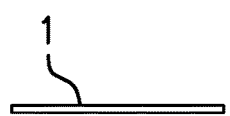
FIG. 9a is a view of an embodiment of the present invention where the spring base is flat.
Figure 9B:
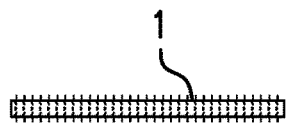
FIG. 9b is an embodiment of the present invention where the spring base is textured.
Figure 9C:
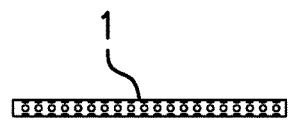
FIG. 9c is an embodiment of the present invention where the spring base is perforated.
Figure 10:
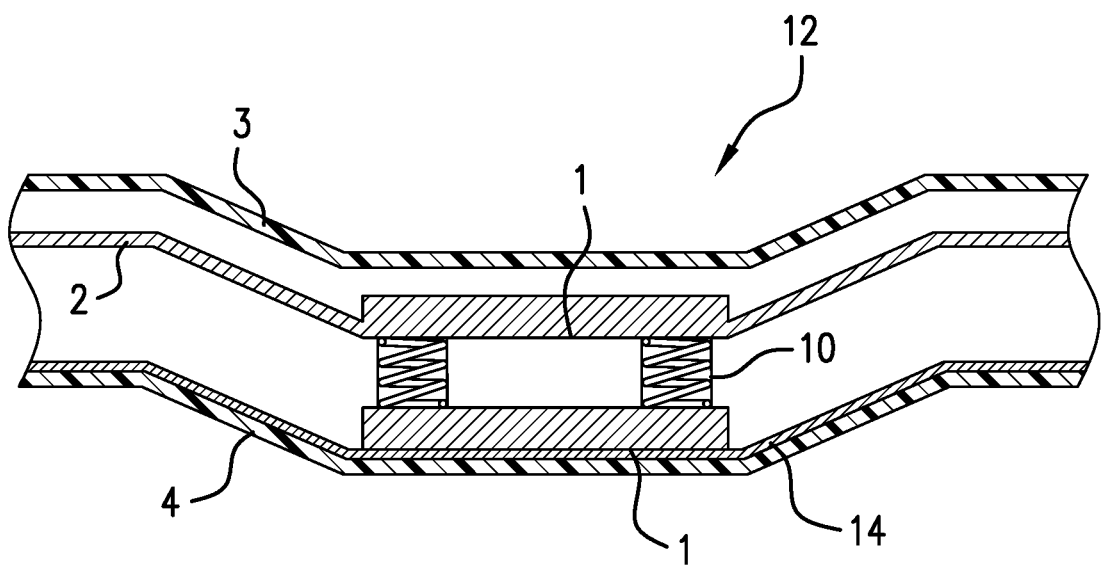
FIG. 10 is a further embodiment of the present invention in which leaf springs comprising one or more spring arms (1) and a spring base (2) are combined with one or more spiral or helical springs and an additional spring base (1).
Figure 11:
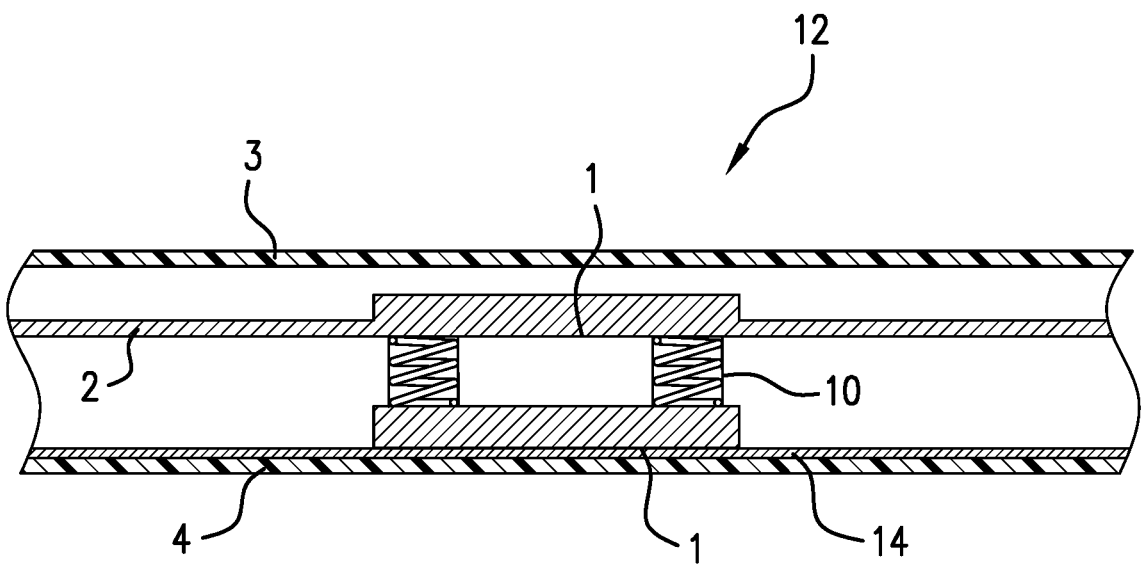
FIG. 11 is a yet further embodiment of the present invention having horizontal spring arms (1), helical springs (10) and a second spring base (2).

In a general embodiment of a scar dressing or bandage (12) with an integrated pressure or force applying spring, such as those given in FIGS. 1-3 and 5-6, the spring can have a spring base (1) that is thinner, equally thick, or thicker than the spring arms (2) spring. The spring base (1) permanently applies pressure to the scar tissue. The spring base (1) can be flat, textured, or perforated, as shown in FIGS. 9a-9c. The spring base (1) may include storage structures (6) in which specific scar creams or scar substances (11) can be packed away. The storage structures (6) can be over-layered with or without a slowly diffusing layer (14), so that a steady release of the scar creams or scar substances is made possible. The arms of the spring (2) are, with application, pressed down onto the skin, and therefore remain in position by the self-adhesive lower carrier layer (4) or the self-adhesive edge of the upper carrier layer (3). By pressing down the arms of the spring (2) onto the level of the skin surface, a permanent pressure is applied to the scar tissue.

The pressure on the scar tissue is preferably permanently at a minimum of 0.0034 N/mm$^2$, 0.0035 N/mm$^2$, preferably 0.005 N/mm$^2$, more preferably 0.01 N/mm$^2$, and even more preferably 0.02 N/mm$^2$. The pressure can be, without limitation, variable upwards. Pressures of up to 0.10 N/mm$^2$ are readily achievable. According to the thickness or the material making up the spring arms (2), any desired permanent pressure can be created on the scar tissue. The pressure is then applied by the spring base (1).

The spring arms (2) may or may not have spring torsion holes (5). Spring torsion holes (5) may be embodied in any desired form, such as cylinders, rhomboids, or slits. Other forms are also possible. The spring arms (2) ensure that sufficient spring force is applied; the spring arms (2), despite their stiffness, conform with the shape of the body. The spring torsion holes (5) can be applied to all or a portion of the spring arms (2) or the spring base (1). The properties of the spring can thereby be lastingly influenced. The spring base (1) and the spring arms (2) must have skin-compatible edges such as rounded off edges (8) or edges with a pillow dressing (9) of accordingly skin-compatible material.

A lower carrier layer (4) is applied below the force applying spring. The lower carrier layer (4) has a scar dressing of breathable matrix that preferably includes a carrier film (14). The carrier film (14) is preferably made of a polymer sheet that is water vapor permeable and water impermeable. Beneath the force applying spring, the lower carrier layer (4) can comprise polyurethane/silicon. Below the force applying spring (1, 2, 10), the lower carrier layer (4) can be perforated with holes (13), in which various scar cream substances (11) can be placed in the storage structures (6) of the spring. The active substance can then be applied simultaneously with the permanent pressure over a long period of time. Below the force applying spring (1, 2, 10), the lower carrier layer (4) can be self-adhesive. By simultaneous pressure and dispensing of cream or other substances (11), a permanent pressure and emulsion treatment of the scar tissue is achieved.

Above the force applying spring is disposed an adhesive, skin-friendly upper carrier layer (3) that surrounds the force applying spring with a sufficiently large adhesive edge, in order to apply the bandage. This adhesive edge holds the bandage or dressing in place so that the pressure is applied by the spring (1, 2) to the scar tissue. The pressure applying spring (1, 2) is preferably made of medical plastic. However, the spring can be made of metal, wood cellulose, non-woven materials, fiber composite materials, or any other desired material.

Example No. 1

Figure 1:
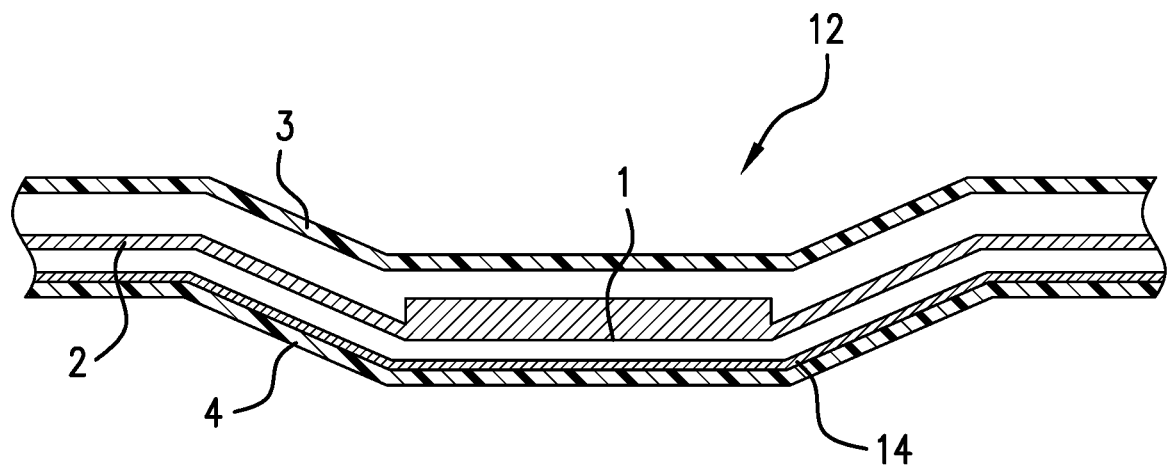
FIG. 1 is a cross sectional view of an embodiment of the present invention.
Figure 2:
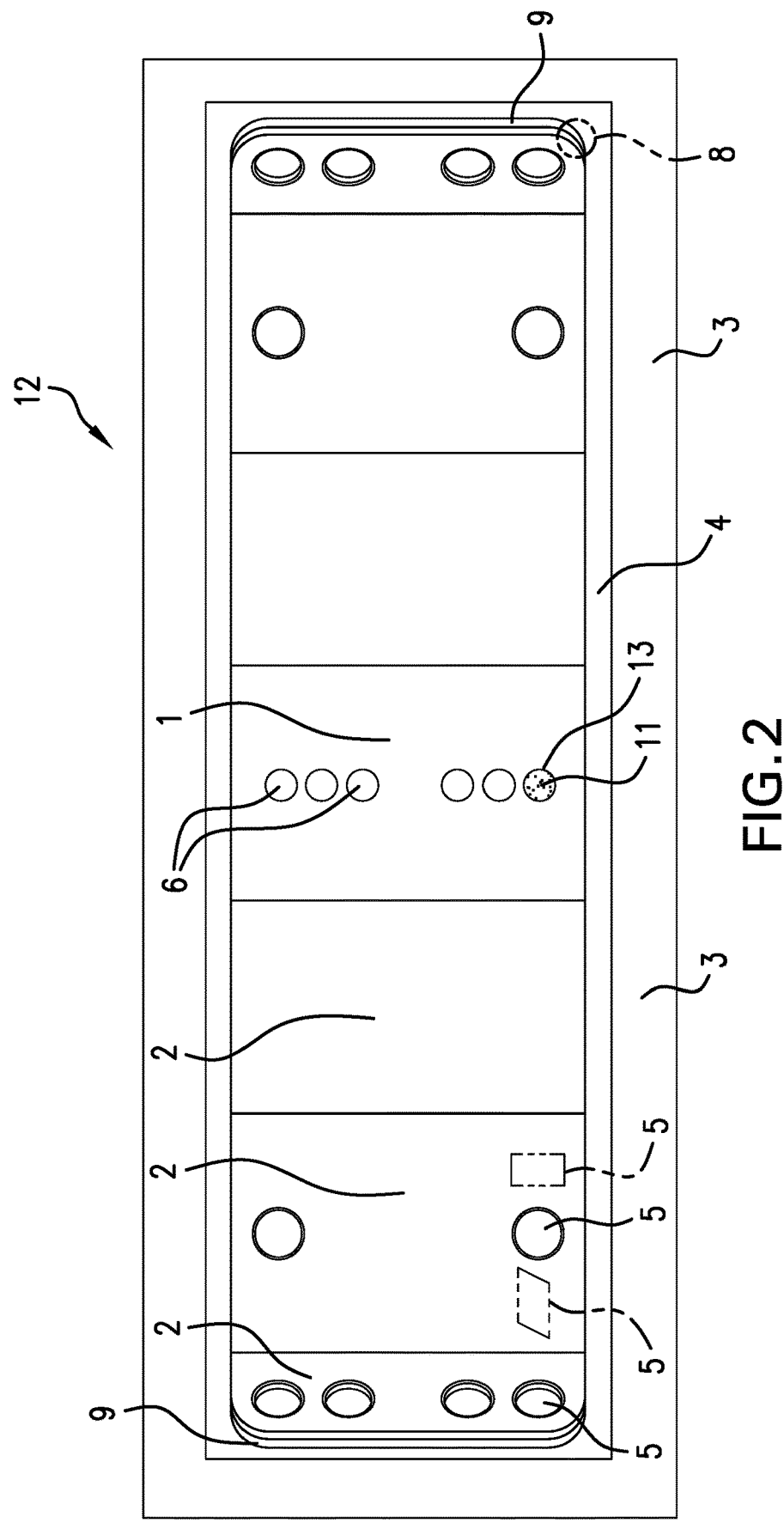
FIG. 2 is a top plan view of an embodiment of the present invention.
Figure 3:
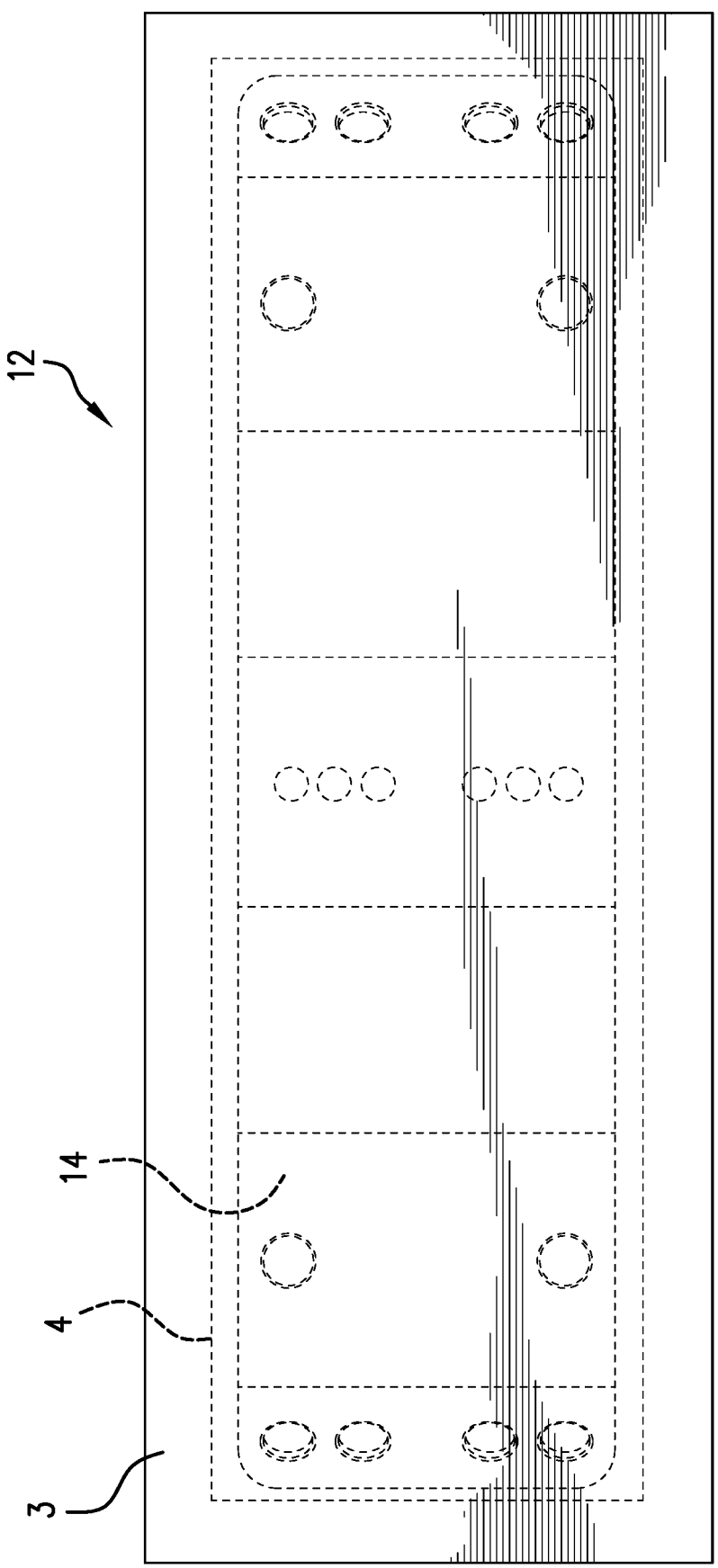
FIG. 3 is an embodiment of the present invention used in the Examples.

A scar reducing bandage or dressing is provided according to the embodiment shown in FIGS. 1-3. To compare the bandage according to the invention with the prior art a conventional bandage comprising a silicon plate with silicon gel is also provided. The bandage in FIGS. 1-3 is easy to use, easy to remove from its packaging and exerts a pressure of from 10 to 100 times the pressure of the conventional bandage, and can be applied water-tightly over a period of months.

Figure 4:
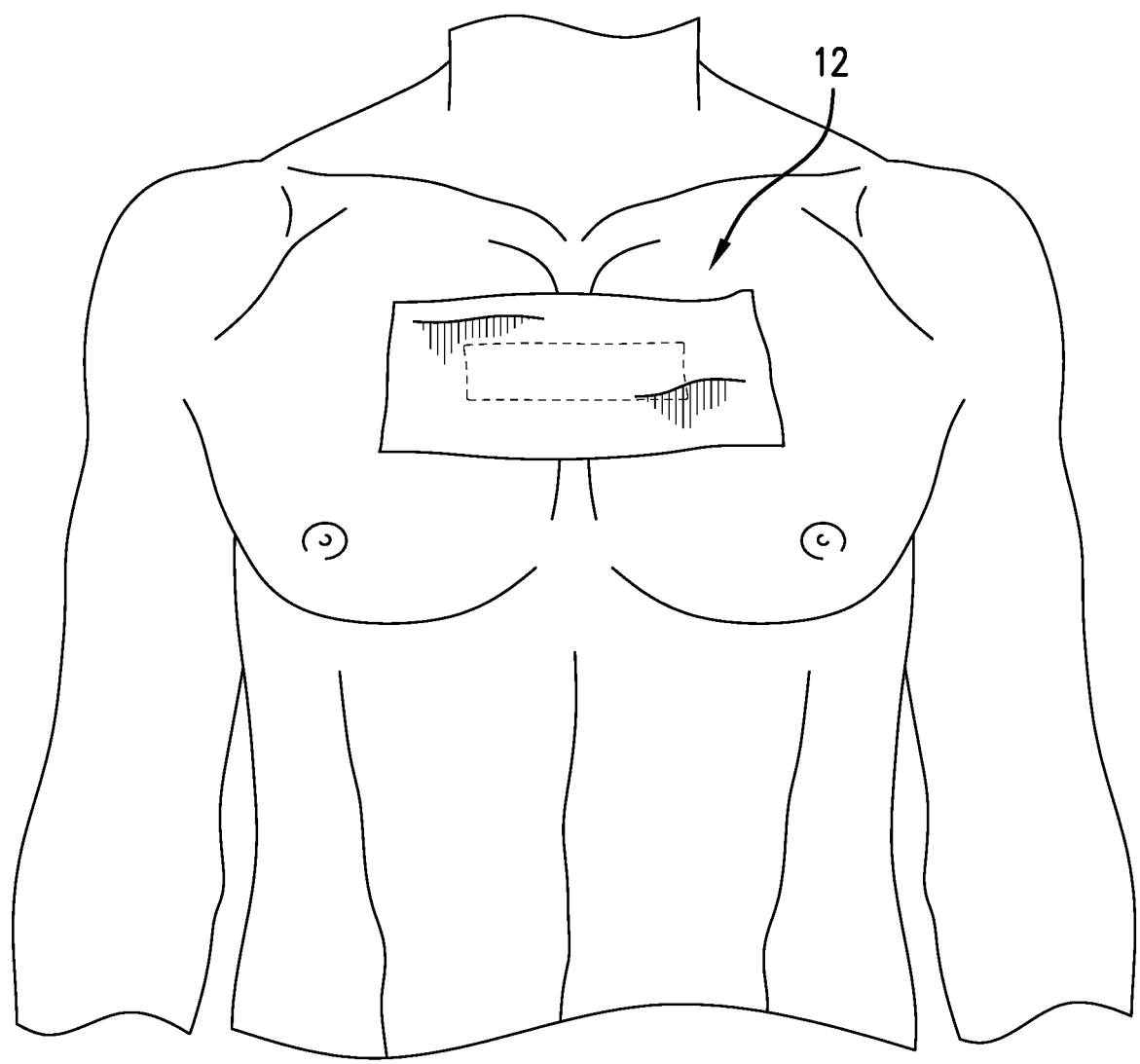
FIG. 4 is an example of the present invention applied to hold a user's skin in place with the skin-friendly adhesive edge while the pressure from the spring(s) is applied in the same position on the spring base.
Figure 5:
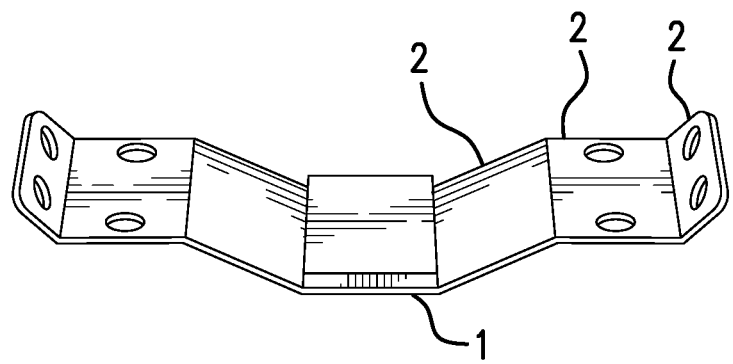
FIG. 5 is a side view of an embodiment of the invention prior to pressing down to apply pressure.
Figure 6:
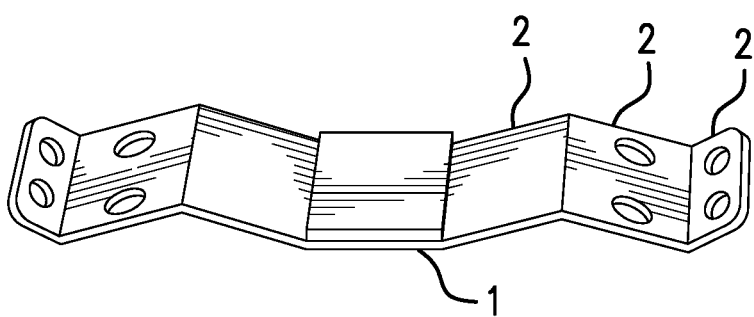
FIG. 6 is a side view of an embodiment of the invention after pressing down to apply pressure.
Figure 7:
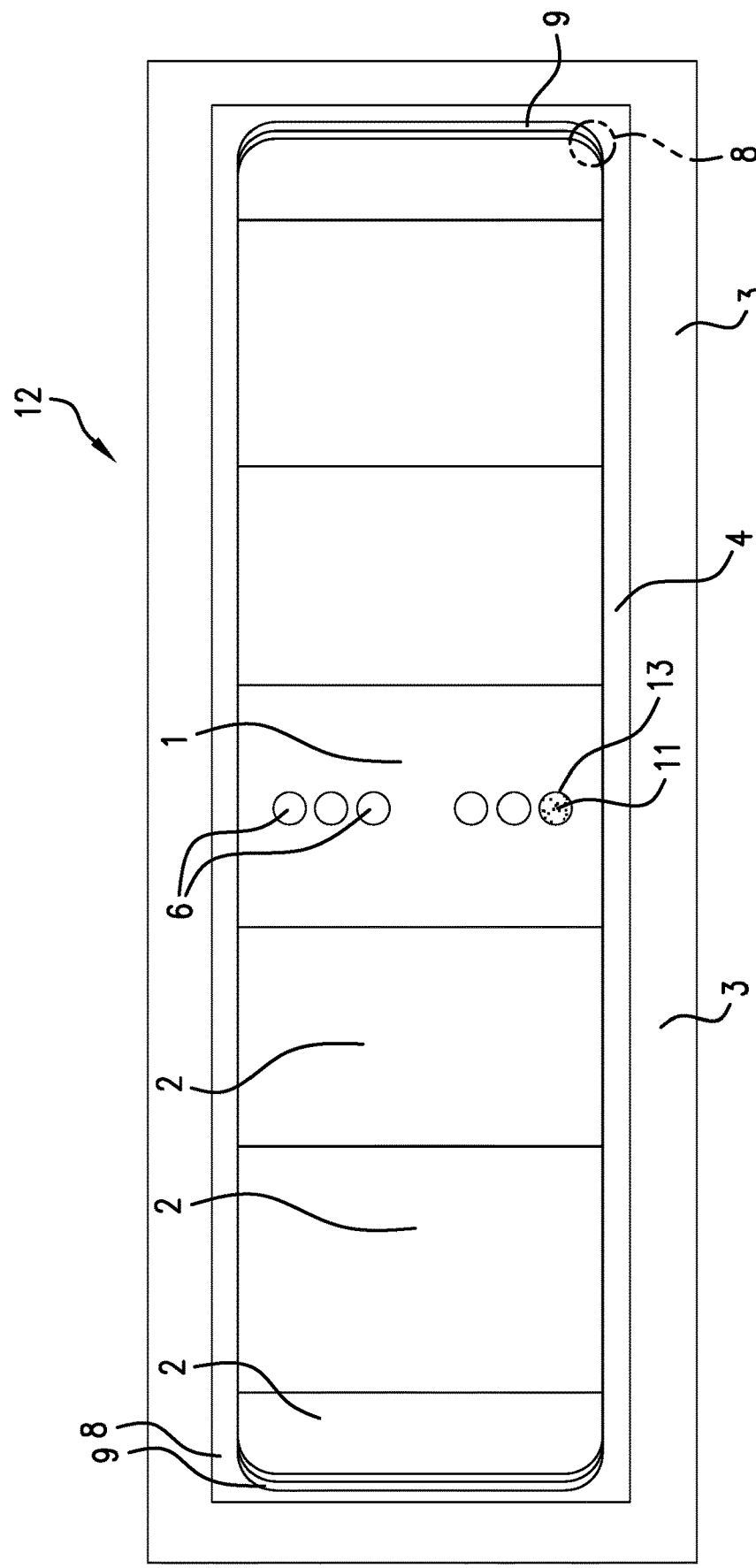
FIG. 7 is an embodiment of the present invention where the lower carrier layer has holes, and there is a slowly diffusing film and a carrier film, and where the springs are spiral springs, and there are no torsion holes.
Figure 8A:
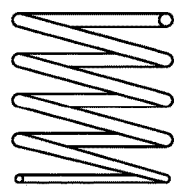
FIG. 8a is a view of one of the springs in an embodiment of the present invention where the spring base is thinner than the actual spring.
Figure 8B:
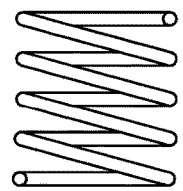
FIG. 8b is a view of one of the springs in an embodiment of the present invention where the spring base is equally thick as the actual spring.
Figure 8C:
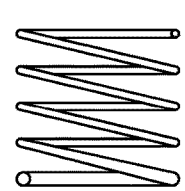
FIG. 8c is a view of one of the springs in an embodiment of the present invention where the spring base is thicker than the actual spring.
Figure 8D:
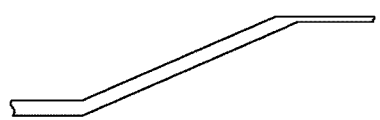
FIG. 8d is a view where the spring base is thicker than the spring arms.
Figure 8E:
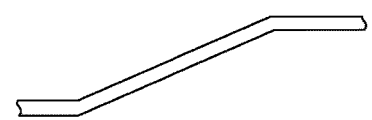
FIG. 8e is a view where the spring base and spring arms are equally thick.
Figure 8F:
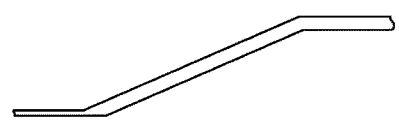
FIG. 8f is a view where the spring base is thinner than the spring arms.
Figure 8G:
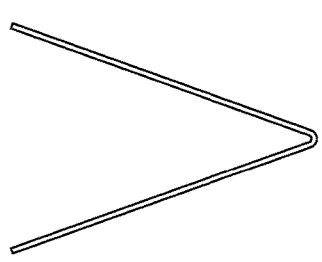
FIG. 8g is a view where the helical springs 10 are replaced with V-shaped leaf springs of one or more layers.
Figure 8H:
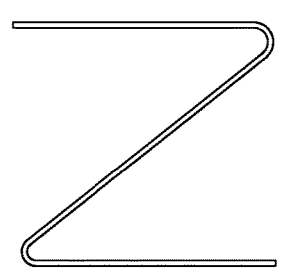
FIG. 8h is a view where the helical springs 10 are replaced with Z-shaped leaf springs of one or more layers.
Figure 8I:
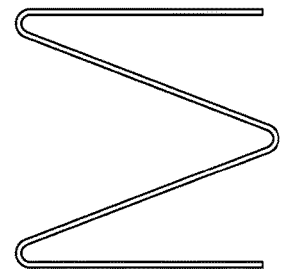
FIG. 8i is a view where the helical springs 10 are replaced with M-shaped leaf springs of one or more layers.

Such comparative conventional bandages are readily available in the marketplace and an example of such conventional bandages is shown in FIG. 4.

Before treatment with the bandage of the present invention an aggressive hypertrophic scar resulting from chicken pox is identified on the sternum of a 8 year old male patient, with mixed skin type, and treated with the conventional bandage having adhesive pressure, silicon pads and massaging. The conventional treatment is unsuccessful. Similar to a keloid, the hypertrophic scar became steadily bigger, in a very prominent section of the sternum.

Before treatment with the bandage of the present invention, the hypertrophic scar had a height of 3.11 mm, was of a hemispherical shape, and had a diameter of approximately 8 mm. After four months of treatment with the bandage of the present invention, scar had decreased to a height of only 1.0 mm. In conclusion the hypertrophic scar in this Example continued to grow in spite of treatment with a conventional bandage including treatment with the silicon pad, massage, and adhesive pressure. Through use of the bandage of the present invention, the scar was reduced by about 2.0 mm.

Example No. 2

A 47 year old male patient was identified with an aggressive keloid on the shoulder after a mosquito bite. Treatment with the conventional bandage, along with a silicon pad, cream, an adhesive pressure bandage and massages was unsuccessful. The keloid continued to grow, itched, and had the feeling of a foreign body. The keloid according to the example had a height of about 4 mm, was of an ovoid shape approximately 20 mm×15 mm, after treatment with the conventional method. After 3.5 months treatment with the bandage according to the present invention, the height of the keloid was reduced to about 1.5 mm. In conclusion, the keloid of the Example continued to grow in spite of treatment with the convention bandage including silicon pads, adhesive pressure bandages and massage. Through use of the bandage of the present invention, the height of the keloid was reduced by approximately 2.5 mm in 3.5 months.

Measurement Pressure of the Spring

The spring according the bandage of the comparative Examples is placed on a scale and force is applied to the spring until it reaches its maximum compression. Compare FIGS. 5 and 6. By use of the weight registered on the scale at the maximum compression, the force is calculated to be 0.02266 N/mm2. This degree of force is approximately a factor of 10 greater than the conventional method.

DRAWING LEGEND

1. Spring base
2. Spring arm
3. Upper carrier layer
4. Lower carrier layer
5. Spring torsion holes
6. Storage structures
7. Slowly diffusing film
8. Rounded edge
9. Pillow edge
10. Helical spring
11. Scar cream or scar substance
12. Bandage
13. Holes
14. Carrier film

What is claimed is:

1. A scar-reducing bandage or dressing for treatment of hypertrophic scars and keloids, the bandage or dressing comprising:
   (a) a spring base;
   (b) one or more pressure-applying springs with each spring having one or more spring arms connected to the spring base, at least one of the spring arms having one or more spring torsion holes defined therein;
   (c) a lower carrier layer comprising a breathable polyurethane matrix; and
   (d) an upper carrier layer that is skin-friendly and adapted to secure the upper carrier to a person's skin, the spring base being disposed between the lower and upper carriers, at least a portion of the lower carrier layer being disposed and adapted to be in contact with the skin of the person when the upper carrier is secured to the person's skin, and the one or more spring arms being adapted to transfer force to the spring base to permanently press the portion of the lower carrier layer in contact with the person's skin against the person's skin when the upper carrier is secured to the person's skin.

2. The bandage or dressing according to claim 1, wherein the one or more springs are integral with the bandage or dressing.

3. The bandage or dressing according to claim 1, wherein the one or more springs are arranged to apply a permanent pressure to a user's scar tissue.

4. The bandage or dressing according to claim 3, wherein the pressure is permanently applied to the user's scar tissue by the spring base at a minimum pressure of 0.0034 N/mm$^2$.

5. The bandage or dressing according to claim 3, wherein the pressure is permanently applied to the user's scar tissue by the spring base at a minimum pressure of 0.005 N/mm$^2$.

6. The bandage or dressing according to claim 3, wherein the pressure is permanently applied to the user's scar tissue by the spring base at a minimum pressure of 0.01 N/mm$^2$.

7. The bandage or dressing according to claim 3, wherein the pressure is permanently applied to the user's scar tissue by the spring base at a minimum pressure of 0.02 N/mm$^2$.

8. The a bandage or dressing according to claim 1, wherein the bandage or dressing is configured to apply pressure permanently to a surface.

9. The bandage or dressing according to claim 1, wherein the one or more springs are arranged to protect a user's scar from UV light.

10. The bandage or dressing according to claim 1, wherein, below the one or more springs, the lower carrier layer of the spring base further comprises polyurethane/silicone.

11. The bandage or dressing according to claim 1, wherein, below the one or more springs, the lower carrier layer has storage structures, wherein the storage structures are loadable with scar cream substances.

12. The bandage or dressing according to claim 11, wherein the storage structures comprise storage holes, and wherein one or more scar cream substances loaded in the storage holes are applicable simultaneously with permanent pressure of the one or more springs.

13. The bandage or dressing according to claim 1, wherein the lower carrier layer is self-adhesive under the one or more springs.

14. The bandage or dressing according to claim 1, wherein the upper carrier layer comprises a skin-friendly adhesive edge or skin-friendly adhesive strips configured to hold a user's skin in position, and wherein permanent pressure from the one or more springs is applied in the same position on the spring base.

15. The bandage or dressing according to claim 1, wherein the lower carrier layer further comprises an adhesive or non-adhesive skin-friendly material configured to hold a user's skin in position, and wherein permanent pressure from the one or more springs is always initiated by the spring base in the same place.

16. The bandage or dressing according to claim 1, wherein the one or more springs are made of a material selected from the group consisting of medical plastic, metal, wood, cellulose, non-woven, and fiber composite materials.

17. The bandage or dressing according to claim 1, wherein the spring base is thinner than the spring itself.

18. The bandage or dressing according to claim 1, wherein the spring base is equally thick as the spring itself.

19. The bandage or dressing according to claim 1, wherein the spring base is thicker than the spring itself.

20. The bandage or dressing according to claim 1, wherein the spring base has a surface that is flat, textured, or perforated.

21. The bandage or dressing according to claim 1, wherein the spring base has storage structures configured to store scar creams or scar substances.

22. The bandage or dressing according to claim 21, wherein the storage structures are covered with a slowly diffusing film, so that a steady or immediate provision of the substances is produced.

23. The bandage or dressing according to claim 1, wherein the pressure is applicable via pressing down the spring arms to a level of an outer surface of a user's skin, and wherein the springs are configured to accommodate a shape of the user's skin.

24. The bandage or dressing according to claim 1, wherein a desired permanent pressure is producible on a user's scar tissue according to a thickness or a material composition of the spring arms, and wherein the pressure is transferable to the scar tissue by the spring base.

25. The bandage or dressing according to claim 1, wherein the spring base has a stiffness selected according to the type of scar or application.

26. The bandage or dressing according to claim 1, wherein each of the spring torsion holes has a form selected from the group consisting of cylinders, rhomboids, or slits.

27. The bandage or dressing according to claim 1, wherein the spring torsion holes are operably arranged to ensure sufficient spring force is applied, wherein the spring arms are stiff, and wherein the spring arms are configured to conform to the shape of a user's skin.

28. The bandage or dressing according to claim 1, wherein the spring base and the spring arms comprise skin-friendly rounded-off edges or edges with pillow applications comprising a skin-friendly material.

29. The bandage or dressing according to claim 28, wherein various small spiral springs are used between the upper carrier layer and the lower carrier layer.

30. The bandage or dressing according claim 1, wherein the plurality of springs, the spring arms, or the spring base is made elastic with stretch joints or slits.

31. The bandage or dressing according to claim 1, wherein the lower carrier layer further comprises a breathable and adhesive polyurethane matrix.

32. The bandage or dressing according to claim 1, wherein the lower carrier layer includes a carrier film made of a polymer that is water vapor permeable and water impermeable.

* * * * *